(12) United States Patent
Mondschein

(10) Patent No.: US 8,535,220 B2
(45) Date of Patent: Sep. 17, 2013

(54) LAPAROSCOPE CLEANING SYSTEM

(76) Inventor: Robert Mondschein, Melville, NY (US)

( * ) Notice: Subject to any disclaimer, the term of this patent is extended or adjusted under 35 U.S.C. 154(b) by 1441 days.

(21) Appl. No.: 12/029,169

(22) Filed: Feb. 11, 2008

(65) Prior Publication Data

US 2008/0200765 A1     Aug. 21, 2008

Related U.S. Application Data

(60) Provisional application No. 60/890,321, filed on Feb. 16, 2007.

(51) Int. Cl.
 *A61B 1/12*      (2006.01)
(52) U.S. Cl.
 USPC ............................ 600/157; 600/158; 600/159
(58) Field of Classification Search
 USPC ................. 600/114, 153, 155–158, 125, 131, 600/159, 169
 See application file for complete search history.

(56) References Cited

U.S. PATENT DOCUMENTS

| | | | | |
|---|---|---|---|---|
| 4,392,485 A * | 7/1983 | Hiltebrandt | ................... | 600/153 |
| 5,103,804 A * | 4/1992 | Abele et al. | ................... | 600/116 |
| 5,518,502 A * | 5/1996 | Kaplan et al. | ................. | 600/157 |
| 5,630,795 A * | 5/1997 | Kuramoto et al. | .............. | 604/30 |
| 6,585,642 B2 * | 7/2003 | Christopher | ................... | 600/156 |

* cited by examiner

*Primary Examiner* — Alireza Nia
(74) *Attorney, Agent, or Firm* — Tutunjian & Bitetto, P.C.

(57) ABSTRACT

A laparoscope lens cleaning system includes a housing that is configured to be connected to existing laparoscopes. The housing forms a lumen which carries a tube for dispensing cleaning solution. An extension system enables the tubing to be extended beyond the end of the laparoscope such that a hole or a plurality of holes in the extended tube end enables the dispensing of cleaning solution on the lens without requiring removal of the laparoscope from the patient. A pumping system is connected to the other end of the tubing and provides a cleaning solution reservoir and means for selectively dispensing the cleaning solution when required by the surgeon.

19 Claims, 4 Drawing Sheets

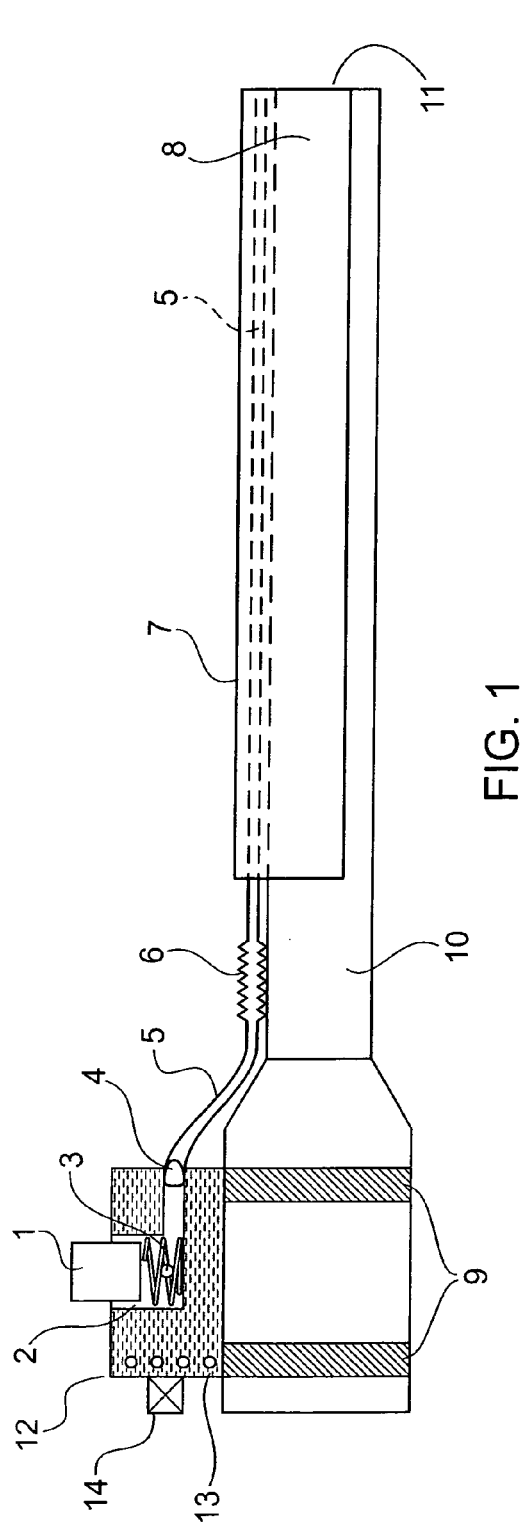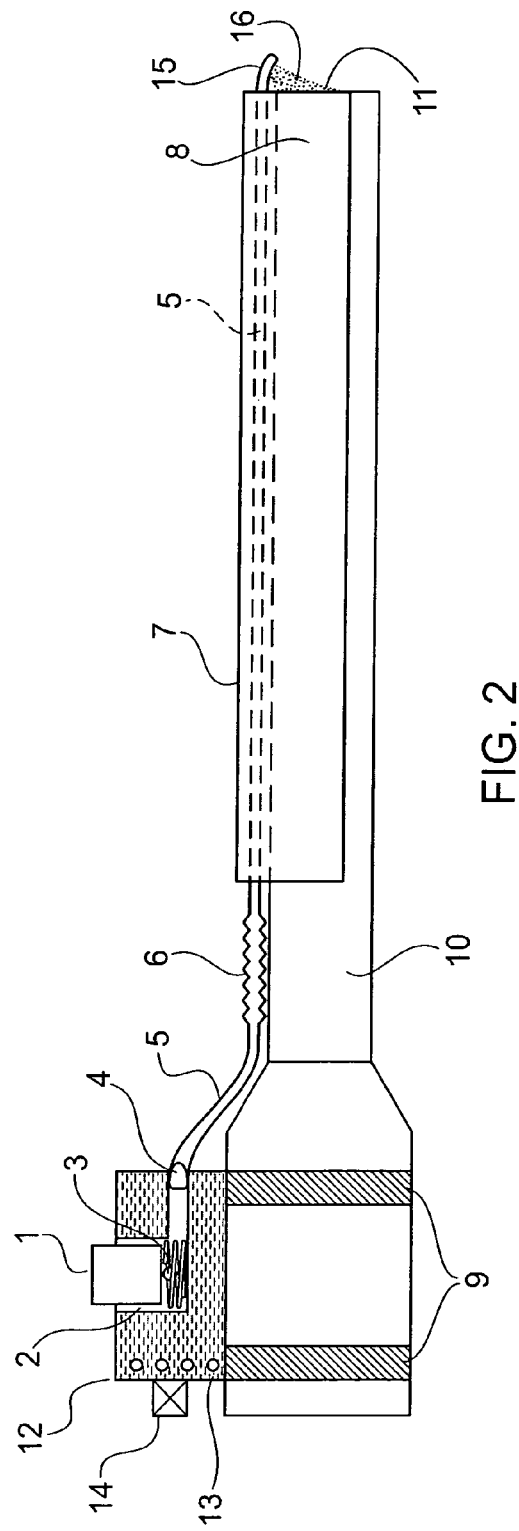

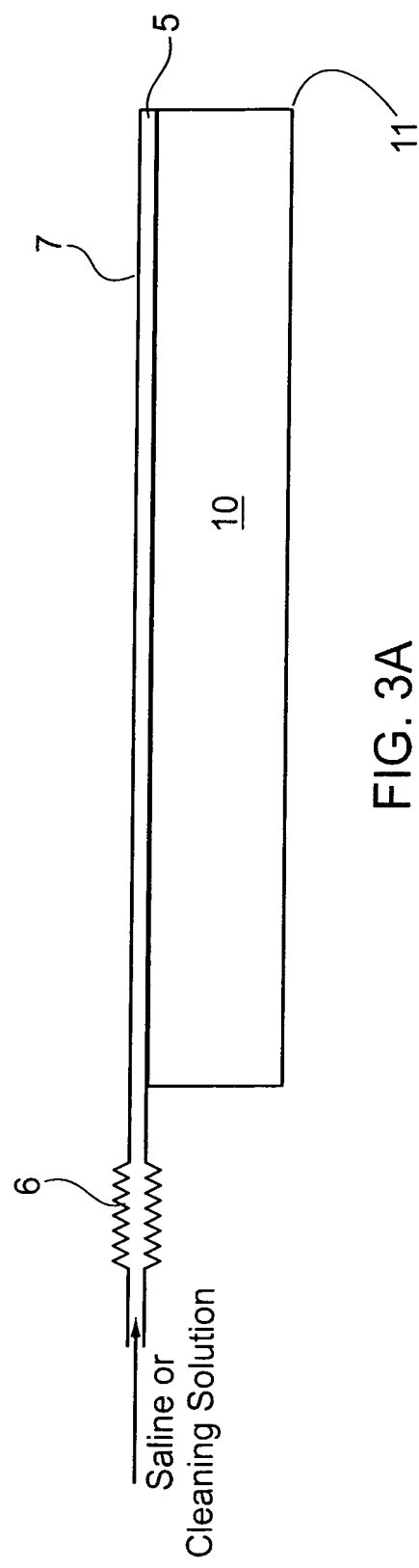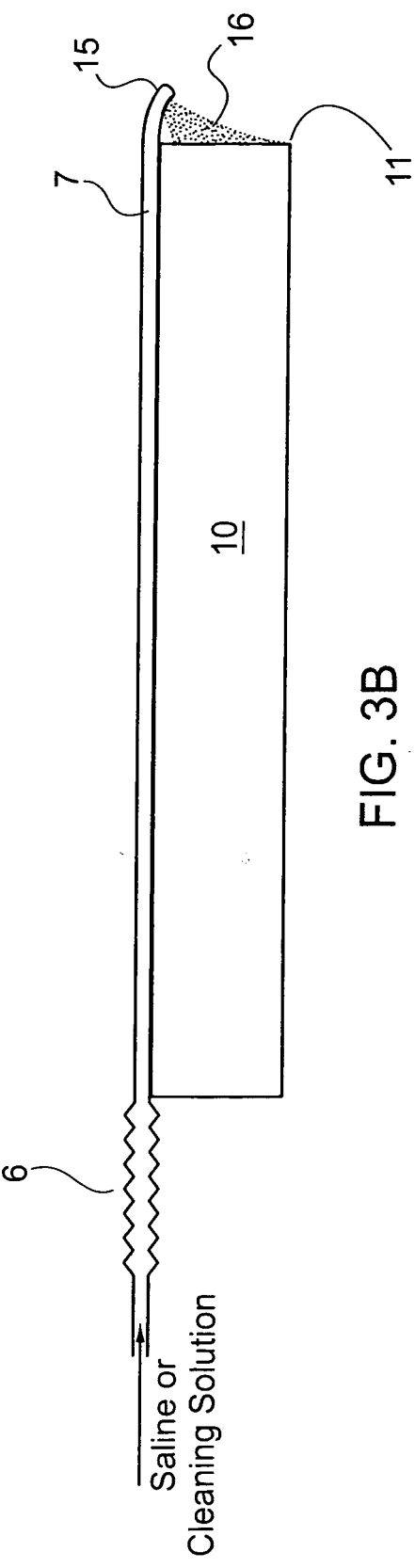

LAPAROSCOPE CLEANING SYSTEM

CROSS REFERENCE TO RELATED APPLICATIONS

This application claims priority from U.S. Provisional Patent Application Ser. No. 60/890,321 filed on Feb. 16, 2007.

BACKGROUND

1. Field of Technology

The present principles relate to surgical procedures which are performed laparoscopically, regardless of the nature or type of the surgery itself. More specifically, they relate to the field of instruments and systems for use in laparoscopic surgery and to methods for using said instruments and systems.

2. Description of Related Art

Laparoscopy has become an extremely common surgical modality in the treatment of various intra-abdominal problems. During laparoscopy, a laparoscope is inserted through a trocar in the abdominal wall.

A laparoscope is a type of endoscope used in minimally invasive surgery (MIS). Laparoscopes are typically used with other surgical instruments to help diagnose and treat various conditions. During laparoscopic procedures, the surgeon inserts the laparoscope and other instruments through one or more small incisions or punctures in the abdominal wall. Laparoscopic surgery is often preferred over traditional open procedures because of the small size of each abdominal incision, reduced postoperative pain, and shorter hospitalization and recovery time.

A laparoscope's optical system employs a series of as many as 20 elements that provide magnification, a wide field of view, and high resolution visualization f the area under treatment. The most common optical design is the rod-lens system, which uses long, closely spaced, rod like lenses. The rod-lens system conveys a bright, detailed image because the rod shaped lens transmits a large amount of reflected light and have a wide angle of view. The lens system, contained within the shaft of the laparoscope, is surrounded by a bundle of illuminating fibers that parallel the long axis of the laparoscope and connect to a light source by means of a flexible fiber optic cable.

One of the problems encountered during the use of laparoscopes is clouding or fogging of the tip thereby preventing clear view and visualization to the surgeon. This problem can occur, for example, when a cool laparoscope is inserted into a warm peritoneal cavity. Fogging can also occur from the condensed moisture in the body cavity. Heating the laparoscope in warm saline solution before insertion currently alleviates lens fogging. The lens of the laparoscope can also be obscured by body fluids, blood or other organic material, including bodily tissues, displaced by the surgical activity.

Currently, surgeons frequently find the lens of the scope requires cleaning to restore maximum visibility. The current procedure for cleaning the scope lens requires removal of the scope from the body, followed by a lens cleaning process, followed by reinsertion of the scope into the body. While the frequency of lens cleaning varies from procedure to procedure, it would be desirable to be able to clean the scope lens while it is inside the body.

The present principles seek to overcome the deficiencies in the art to provide improved apparatus and methods for cleaning a laparoscope lens during a procedure without requiring removal of the laparoscope lens from the body.

The apparatus and methods described herein are applicable to any laparoscopic devices, including endoscopes, currently known and used in the art, or any improvements thereto. For example, laparoscopic devices that can be used with the apparatus and methods of the present principles include, but are not limited to, those by Applied Medical Technologies, Cook Endoscopy, Ethicon Endo-Surgery, H.M.B. Endoscopy Products, Horizons International Corp., InScope, Integrated Medical Systems International, Inc., Karl Storz Endoscopy, Olympus Medical Endoscope & Surgical Products, Pentax Medical, Smith & Nephew Endocopy, Spirus Medical, Stryker Endoscopy, US Endoscopy, and US Surgical. Furthermore, those devices described in U.S. Pat. Nos. 4,148,550, 4,148,551, 4,440,157, 4,576,147, 4,610,242, 4,617,933, 4,624,243, 4,742,818, 4,745,470, 4,779,613, 4,854,302, 4,919,112, 4,964,710, 5,114,422, 5,190,028, 5,278,642, 5,299,560, 5,352,237, 5,359,453, 5,369,525, 5,412,504, 5,416,634, 5,447,148, 5,458,133, 5,538,496, 5,634,881, 5,817,015, 5,954,637, 6,120,434, and 6,387,044 can also be used with the apparatus and methods of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

SUMMARY

It is an aspect of the present principles to provide an apparatus adaptable for use with multiple laparoscopes and a method of use thereof which will allow a surgeon to clean the laparoscope while the laparoscope is inside the body.

Another aspect of the present principles it to provide a cleaning accessory or apparatus that is attached to an existing laparoscope and inserted via the trocar into the abdominal wall. At the proximal end of the laparoscope, a reservoir will contain heated fluid which, upon activation, is forced down the length of the laparoscope to the distal end where the fluid will be directed onto the lens in order to accomplish the cleaning.

According to one implementation, the laparoscope lens cleaning system includes a housing connectable to a laparoscope, a tubing contained within the housing and having a first end and a second distal end, the tubing being configured to have the second end extendable beyond an end of the laparoscope, means for extending the second distal end of the tubing, a cleaning solution reservoir connected to the first end of the tubing, and means for dispensing the cleaning solution onto the lens of the laparoscope during use of the laparoscope.

Other aspects and features of the present principles will become apparent from the following detailed description considered in conjunction with the accompanying drawings. It is to be understood, however, that the drawings are designed solely for purposes of illustration and not as a definition of the limits of the present principles, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference numerals denote similar components throughout the views:

FIG. 1 is a side view of the laparoscopic cleaning apparatus, attached to a laparoscope with the cleaning apparatus in the retracted position, according to an implementation of the present principles;

FIG. 2 is a side view of the laparoscopic cleaning apparatus as attached to a laparoscope with the cleaning apparatus in the extended position, according to an implementation of the present principles.

FIG. 3A is a side view of the laparoscopic cleaning apparatus, in a retracted position, according to another implementation of the present principles;

FIG. 3B is a side view of the laparoscopic cleaning apparatus, as attached to the laparoscope, in an extended position, according to the implementation of FIG. 3A;

DETAILED DESCRIPTION

Figure 4A:
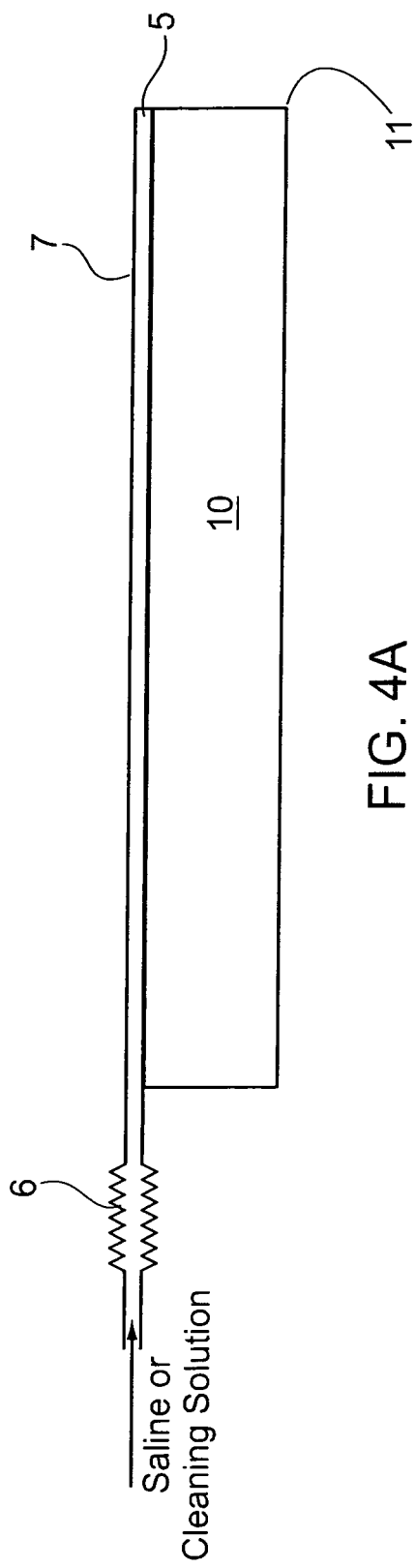
FIG. 4A is a side view of the laparoscopic cleaning apparatus, in a retracted (home) position, according to yet another implementation of the present principles.

The present principles relate to an apparatus which will allow a surgeon to clean the laparoscope while the laparoscope is inside the body.

In one implementation of the present principles, the apparatus is attached to the laparoscope and ad enables the direction of fluid onto the lens when activated. The apparatus can be removably attached to the laparoscope, or alternatively, the apparatus can be integrated into the laparoscope assembly. Where the apparatus is removably attached to the laparoscope, it apparatus may be attached to the same by any suitable known means, including but not limited to, snap fit assemblies, hook and loop fasteners, tongue-in groove mechanisms, magnetic fasteners, screw-on assemblies, adhesives, and the like.

The apparatus can be made of materials including, but not limited to, plastics (e.g., polyurethanes, ABS plastic, etc), stainless steel, titanium, nitinol, and any other suitable known material for use in a surgical environment.

In another implementation, the apparatus includes a reservoir for holding fluid (e.g., a cleaning solution), means for moving the fluid to the distal end of the laparoscope, and means for directing the fluid towards the lens of the laparoscope. The reservoir can include means for easily refilling the same while the apparatus is in use. The reservoir can additionally include means for determining the level of fluid remaining in the reservoir, such as a visual marker or other output indicator designed to indicate the fluid level within the reservoir. In another contemplated implementation, the reservoir can include means for heating the fluid or for maintaining a desired temperature of the fluid.

The means for moving for the fluid to the distal end of the laparoscope can include a pumping chamber connected to the fluid reservoir and operably engaged with a plunger or other activation means, and tubing which extends from said pumping chamber distally along the length of the laparoscope. The pumping chamber may include any known system for causing the movement of a fluid from one location to another, and is not limited by the examples described herein. Those of skill in the art will recognize that the tubing can be made of any suitable known material that can be used during a surgical procedure, and particularly for insertion into a human body. Alternatively, those of skill in the art will also recognize that the tubing function can replaced with an integrated enclosed conduit or the like within the cleaning apparatus.

In one implementation, depression of the plunger or engagement of alternative activation means causes the fluid to be moved distally through the tubing or other means of fluid movement.

In another implementation of the present principles, the means for moving the fluid to the distal end of the laparoscope additionally includes a bellows. The depression of the plunger causes movement of the bellows, thereby causing the fluid to be moved distally through the tubing. The bellows can utilize positive or negative air pressure to move the fluid. Alternatively, or in addition, the bellows can be utilized to increase or decrease the length of tubing extending distally down the laparoscope. In another implementation, the lengthening of the tubing can result in the tubing overhanging or extending beyond the end of the laparoscope so as to enable the "spraying" of cleaning solution onto the laparoscope lens.

In a further implementation, the means for moving the fluid to the distal of end of the laparoscope can include an electrical or mechanical switch. In yet a further implementation, activation of the means for moving the fluid to the distal end of the laparoscope can additionally include movement of the tubing along the length of the laparoscope to result in the tubing overhanging or extending beyond the end of Laparoscope.

In another implementation of the present principles, depression of the plunger causes activation of the mechanical switch, thereby causing the fluid to be moved distally through the tubing. Alternatively or in addition, the depression of the plunger can cause activation of the electrical switch, thereby causing the fluid to be moved distally through the tubing.

The lengthening or movement of the tubing to extend over the distal end of the laparoscope can be caused by depression of the plunger, activation of a mechanical switch, activation of an electrical switch, a bellows, or other means of inducing movement that are known to those of skill in the art, or any combination thereof.

In yet another implementation of the present principles, the lengthening or movement of the tubing to result in the tubing overhanging or extending beyond the end of laparoscope can result in the exposure of one or more openings or holes in the tubing beyond the length of the laparoscope. The openings or holes in the tubing can dispense the cleaning solution when the apparatus is activated. In yet another implementation, the one or more holes or openings can have both a closed and open position which can be controlled by the operator. In one implementation, the one or more openings or holes are placed to direct the flow of cleaning solution. For example, the one or more openings can direct the flow of cleaning solution at the lens of the laparoscope, or a plurality of openings or holes can be placed to direct multiple streams of cleaning fluid at the lens simultaneously in order to maximize the area of the lens which receives the cleaning fluid. In one implementation, the one or more openings or holes results in a spray of cleaning fluid directed at the lens. In another implementation, the one or more openings or holes results in a streaming or dripping of cleaning fluid onto the lens, optionally such that the fluid is dispensed in the same plane as the lens.

It is additionally within the scope of the present principles that the tubing can be stationary along the length of the Laparoscope, such that activation of the cleaning apparatus results in the forcing of cleaning liquid through the tubing to the distal end of the laparoscope and/or the opening of one or more openings or holes in the distal end of the tubing. The stationary tubing can extend over the end of the laparoscope or remain even with the end of the laparoscope. The tubing can include one or more openings or holes placed to direct cleaning fluid at the laparoscope lens. The one or more holes or openings can have both a closed and open position which can be controlled by the operator. For example, the one or more openings can direct the flow of cleaning solution at the lens of the laparoscope, or a plurality of openings or holes can be placed to direct multiple streams of cleaning fluid at the lens simultaneously in order to maximize the area of the lens which receives the cleaning fluid. In one implementation, the one or more openings or holes results in a spray of cleaning fluid directed at the lens. The one or more openings or holes results in a streaming or dripping of cleaning fluid onto the lens, optionally such that the fluid is dispensed in the same plane as the lens.

Referring to FIG. 1, there is shown a laparoscope 10 having the cleaning apparatus housing 8 attached thereto. The cleaning apparatus described herein can include a nozzle (not shown) attached to the distal end of the tubing, wherein the cleaning of the laparoscope lens 11, such that a lumen 7 is created between the top of the laparoscope 10 and the interior of the apparatus housing 8. The tubing 5 extends the length of the laparoscope 10 to its distal end. The tubing 5 extends through the lumen 7 (formed by housing 8) along the length of the laparoscope 10. The tubing 5 may additionally include or be attached to a bellows 6 for dispensing cleaning solution. The cleaning apparatus may further comprise a heating element 13 which is operably engaged to heat or maintain the temperature of the reservoir 12 and the fluid contained therein. In one embodiment, the heating element 13 will be within a cleaning solution reservoir 12. The cleaning apparatus may further contain one or more electromechanical switches and a power source, including a battery or A/C adaptor, which can be operably engaged to operate the bellows 6 or to control the heating element 13.

In use, an embodiment of the present invention as depicted in FIG. 1 provides that depression of the plunger 1 causes an aperture 3 to allow fluid to pass from the reservoir 12 to the pumping chamber 2. The nozzle 4 concentrates the stream of fluid and engages die tubing 5 thru which the fluid passes. The bellows 6 attached to the tubing 5 controls the lengthening or extension of the tubing 5 along the length of the laparoscope 10, wherein the tubing 5 passes thru a lumen 7 within the housing 8.

With specific reference to FIG. 2 as an example of a particular embodiment of the present invention, wherein the cleaning apparatus is activated, there is provided a laparoscope 10 having a lens 11 at the distal end. Attached to the laparoscope 10 by hook and loop fasteners 9 and optionally via a housing 8 is a cleaning apparatus comprising a reservoir-plunger assembly that contains two chambers, a reservoir 12 and a pumping chamber 2. The cleaning apparatus may further comprise a heating element 13 which is operably engaged to heat or maintain the temperature of the reservoir 12 and the fluid contained therein. In one embodiment, the heating element 13 will be within the reservoir 12. The cleaning apparatus may further contain one or more electromechanical switches and a power source, including a battery or A/C adaptor, which can be operably engaged to operate the bellows 6 or to control the heating element 13. The plunger 1 is operably connected to the pumping chamber 2 which operably engages an aperture 3 that controls the release of fluid from the reservoir 12. The aperture 3 regulates the flow of fluid from the reservoir 12 into the pumping clamber 2, from which it is passed to a nozzle 4, which is removably attached to a tubing 5. The nozzle 4 and tubing 5 may be removably attached by means of a threaded screw system, a snap fit system, or other means known to those of skill in the art.

The cleaning apparatus can comprise a housing 8 which s configured to snap onto and be releasably connected to all or a portion of the laparoscope 10, such that a lumen 7 is created between the top of the laparoscope and the interior of the housing 8. The housing further contains the tubing 5 which now extends the length of the laparoscope 10 to the distal end while passing through the lumen 7. The bellows 6 is attached to the tubing 5, such that operation of the bellows functions to extend and retract the tubing 5 over the distal end of the laparoscope 10 as is depicted by the over hang area 15 in FIG. 2. The extended or overhanging portion 15 of tubing 5 directs the cleaning solution 16 onto the lens 11 of the laparoscope 10 following depression of the plunger 1.

With reference to FIGS. 3A and 3B, the tubing 5 assembly is depicted with the bellows 6 in a "home" or contracted position (FIG. 3A) and in an extended position (FIG. 3B). FIGS. 3A and 3B show the lumen 7 formed by the housing 8, which has been removed from these figures for purposes of this description. When the bellows 6 is contracted, the tubing 5 extends distally along the laparoscope 10 (FIG. 3A). Upon activation, the bellows 6 extends, thereby causing the tubing 5 to be in an extended position 15 over the end of the laparoscope 10 (FIG. 3B). The extended portion 15 of the tubing allows the dispensing of cleaning fluid 16 onto the lens 11 (FIG. 3B). In one embodiment of the invention, the tubing 5 can include a curved portion at the distal end such that when extended, the tubing 5 will curve at an angle over the edge of the laparoscope 10 to present the openings or holes in the tubing towards the lens 11 (See FIG. 3B).

Figure 4B:
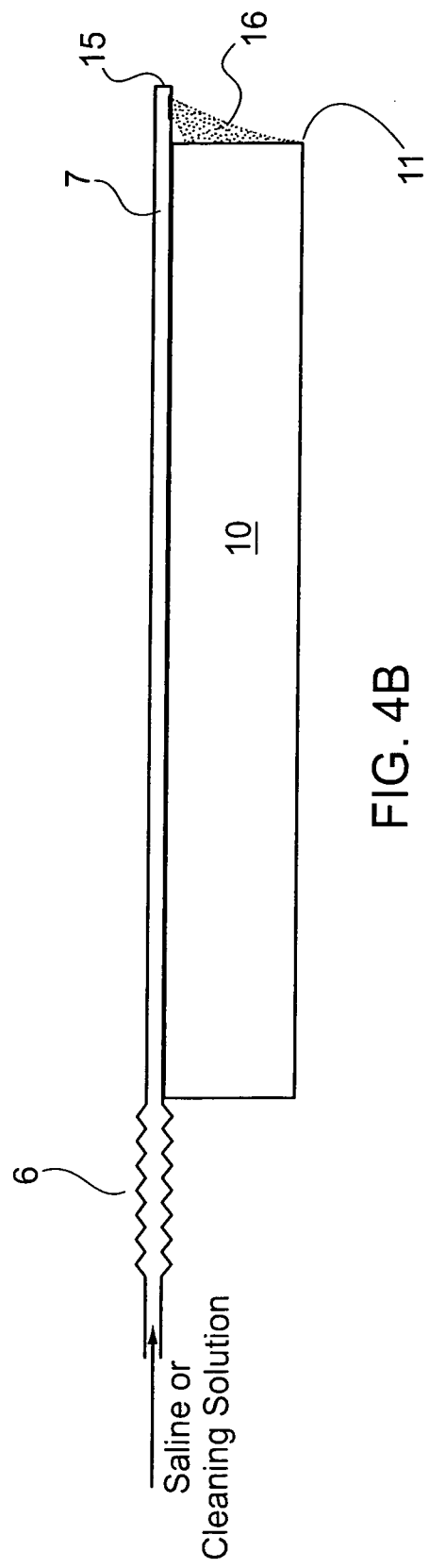
FIG. 4B is a side view of the laparoscopic cleaning apparatus, as attached to the laparoscope, in an extended (actuated) position, according to the implementation of FIG. 4A.

With reference to FIGS. 4A and 4B, the tubing 5 assembly is depicted with the bellows 6 in a "home" or contracted position (FIG. 4A) and in an extended position (FIG. 4B). When the bellows 6 is contracted, the tubing 5 extends distally along the laparoscope 10 (FIG. 4A). Upon activation, the bellows 6 extends, thereby causing the tubing 11 to be in an extended position 15 over the end of the laparoscope 10 (FIG. 4B). The extended tubing 15 allows the dispensing of cleaning fluid 16 onto the lens 11 (FIG. 4B). In one embodiment of the invention, the tubing 5 can be rigid or semi-rigid at the distal end such that when extended, the extended portion 15 of the tubing 5 will extend over the edge of the laparoscope 10 parallel to the upper edge of the laparoscope, such that the extended portion 15 remains straight and the openings or holes in the tubing 5 are exposed to the lens by virtue of their movement outwards from the distal end of the laparoscope 10, and cleaning fluid 16 can then be released onto the lens 11.

Figure 5:
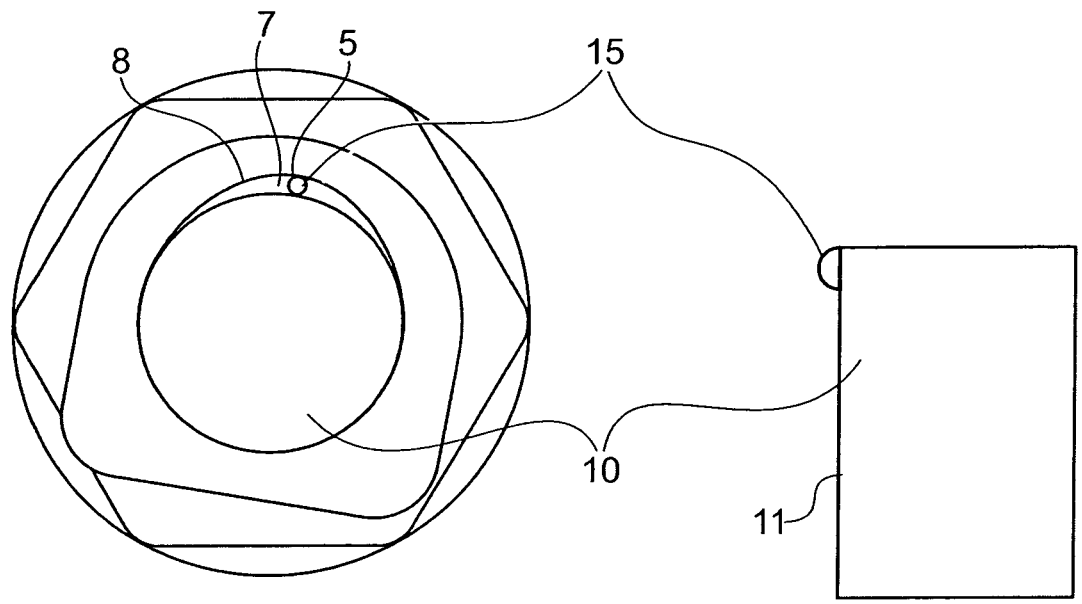
FIG. 5 is a profile view of the laparoscopic cleaning apparatus as attached to a laparoscope.
Figure 6:
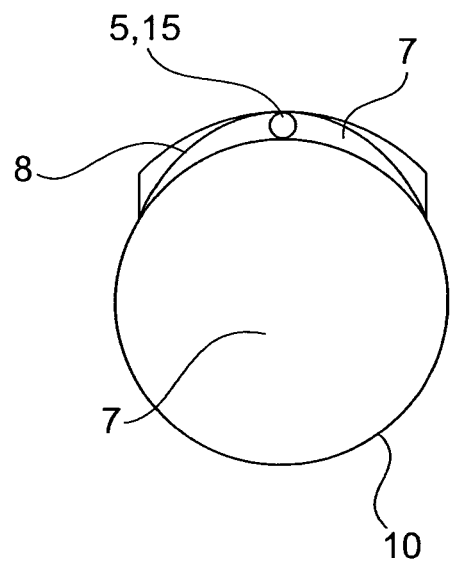
FIG. 6 is a profile view of the laparoscopic cleaning apparatus as attached to a laparoscope.

With reference to FIG. 5 and FIG. 6, profile views of the laparoscope 10 having the cleaning apparatus attached thereto are provided. The profile views depict the housing 8 which creates a lumen 7 between the interior surface of the housing 8 and the outer surface of the laparoscope 10 wherein the tubing 5 extends along the length of the laparoscope 10 within the lumen 8.

In one implementation, a method of performing laparoscopic surgery is provided, wherein the laparoscope has attached thereto a laparoscope cleaning apparatus as described herein, such that the lens of the laparoscope can be cleaned during the surgical procedure without necessitating removal of the laparoscope from the patient's body.

In a further implementation, a method of cleaning a laparoscope lens during a surgical procedure is provided, wherein the method comprises administering cleaning fluid to the lens of the laparoscope via tubing which extends distally along the length of said laparoscope.

In yet a further implementation, a method of cleaning a laparoscope lens during a surgical procedure is provided, wherein the method comprises utilizing a laparoscope cleaning apparatus as described herein.

The cleaning accessory for laparoscopes, as disclosed herein, is configured to provide a lens cleaning capability to scopes that do not have such features, and does so without interfering with the operation of the scope and/or the trocar that may be used to assist in the insertion of the scope into the patient.

While there have been shown, described and pointed out fundamental novel features of the present principles, it will be understood that various omissions, substitutions and changes in the form and details of the methods described and devices illustrated, and in their operation, may be made by those skilled in the art without departing from the spirit of the same. For example, it is expressly intended that all combinations of those elements and/or method steps which perform substantially the same function in substantially the same way to achieve the same results are within the scope of the present principles. Moreover, it should be recognized that structures and/or elements and/or method steps shown and/or described in connection with any disclosed form or implementation of the present principles may be incorporated in any other disclosed, described or suggested form or implementation as a general matter of design choice. It is the intention, therefore, to be limited only as indicated by the scope of the claims appended hereto.

What is claimed is:

1. A laparoscope lens cleaning system comprising:
   a housing connectable to an external surface of a laparoscope, said housing partially enclosing and being configured to receive and release the laparoscope;
   a tubing contained within the housing and having a first proximal end and a second distal end, the tubing being configured to have the second end extendable beyond an end of the laparoscope;
   means for extending the second distal end of the tubing;
   a cleaning solution reservoir connected to the first proximal end of the tubing, said reservoir comprising a chamber configured to be connectable to the external surface of the laparoscope; and
   means for dispensing a cleaning solution onto a lens of the laparoscope during use of the laparoscope, wherein said means for extending comprises a bellows integrated within the proximal end of the tubing, said bellows operable to extend the tubing in response to activation of the dispensing means.

2. The laparoscope lens cleaning system according to claim 1, wherein the reservoir further comprises a heating element for heating cleaning solution contained in the reservoir.

3. The laparoscope lens cleaning system according to claim 1, wherein said dispensing means comprises:
   a pumping chamber in communication with the reservoir and the first end of the tubing; and
   a pumping device in communication with the pumping chamber and configured to cause the cleaning solution to be transferred from the reservoir to the second end of the tubing.

4. The laparoscope lens cleaning system according to claim 1, wherein said second distal end of the tubing comprises at least one hole positioned to release cleaning solution onto the laparoscope lens.

5. The laparoscope lens cleaning system according to claim 1, wherein said second distal end of the tubing comprises a curved portion having at least one hole for dispensing cleaning solution, said curved portion being positioned beyond the end of the laparoscope for cleaning solution dispensing by the extending means.

6. The laparoscope lens cleaning system according to claim 3, wherein said pumping device comprises a mechanical plunger.

7. The laparoscope lens cleaning system according to claim 3, wherein said pumping device comprises an electrical pump device and a power source for providing power to the pump.

8. The laparoscope lens cleaning system according to claim 3, wherein said pumping device comprises an electromechanical switch and a power source for providing power to the switch.

9. A laparoscope lens cleaning system comprising:
   a housing connectable to an external surface of a laparoscope and forming a lumen between the laparoscope and the housing, said housing partially enclosing and being configured to receive and release the laparoscope;
   a tubing contained within the lumen and having a first proximal end and a second distal end, the tubing being configured to have the second end extendable beyond a lens of the laparoscope;
   means for extending the second distal end of the tubing to a point in front of the lens of the laparoscope;
   a cleaning solution reservoir in communication with the first proximal end of the tubing, said reservoir comprising a chamber configured to be connectable to the external surface of the laparoscope; and
   means for dispensing a cleaning solution onto the lens of the laparoscope during use of the laparoscope, wherein said means for extending comprises a bellows integrated within the proximal end of the tubing, said bellows operable to extend the tubing in response to activation of the dispensing means.

10. The laparoscope lens cleaning system of claim 9, wherein the cleaning solution reservoir further comprises a heating element for heating cleaning solution contained in the reservoir prior to dispensing the cleaning solution.

11. The laparoscope lens cleaning system of claim 9, wherein the second distal end of the tubing comprises at least one hole positioned to release cleaning solution onto the laparoscope lens.

12. The laparoscope lens cleaning system of claim 9, wherein the second distal end of the tubing comprises curved portion having at least one hole for dispensing cleaning solution.

13. The laparoscope lens cleaning system according to claim 9, wherein said dispensing means comprises:
   a pumping chamber in communication with the reservoir and the first end of the tubing; and
   a pumping device in communication with the pumping chamber and configured to cause the cleaning solution to be transferred from the reservoir through the tubing to the second distal end.

14. The laparoscope lens cleaning system of claim 1, wherein the housing is configured to snap onto the external surface of the laparoscope.

15. The laparoscope lens cleaning system of claim 9, wherein the housing is configured to snap onto the external surface of the laparoscope.

16. The laparoscope lens cleaning system of claim 1, wherein the reservoir includes a fastener configured to attach to the external surface of the laparoscope.

17. The laparoscope lens cleaning system of claim 16, wherein the fastener comprises a hook and loop fastener.

18. The laparoscope lens cleaning system of claim 2, wherein the heating element is within the reservoir and is operably engaged to heat or maintain the temperature of the reservoir or fluid contained therein.

19. The laparoscope lens cleaning system of claim 3, wherein the pumping chamber and the pumping device are located in the reservoir.

* * * * *